United States Patent
Allen et al.

(10) Patent No.: US 10,786,660 B2
(45) Date of Patent: Sep. 29, 2020

(54) OCCLUSION BALLOON CATHETER AND METHODS OF FABRICATION AND USE

(71) Applicant: Embolx, Inc., Sunnyvale, CA (US)

(72) Inventors: Michael P. Allen, Los Altos, CA (US); Greg Halstead, Sunnyvale, CA (US)

(73) Assignee: Embolx, Inc., Sunnyvale, CA (US)

( * ) Notice: Subject to any disclaimer, the term of this patent is extended or adjusted under 35 U.S.C. 154(b) by 0 days.

(21) Appl. No.: 15/413,262

(22) Filed: Jan. 23, 2017

(65) Prior Publication Data

US 2017/0232239 A1 Aug. 17, 2017

Related U.S. Application Data

(63) Continuation of application No. 15/044,864, filed on Feb. 16, 2016, now Pat. No. 9,550,046.

(51) Int. Cl.
*A61M 25/10* (2013.01)
*A61M 25/00* (2006.01)
*A61M 5/00* (2006.01)

(52) U.S. Cl.
CPC ........ *A61M 25/1025* (2013.01); *A61M 5/007* (2013.01); *A61M 25/005* (2013.01); *A61M 25/1034* (2013.01); *A61M 25/0043* (2013.01); *A61M 2025/0004* (2013.01); *A61M 2025/0042* (2013.01); *A61M 2025/105* (2013.01); *A61M 2025/1061* (2013.01)

(58) Field of Classification Search
CPC .......... A61M 25/0043; A61M 25/1025; A61M 25/1034; A61M 25/104; A61M 2025/0004; A61M 2025/0006; A61M 2025/0039; A61M 2025/0042; A61M 2025/1061; A61M 25/0009; A61M 25/0014
See application file for complete search history.

(56) References Cited

U.S. PATENT DOCUMENTS

| 4,581,017 A | 4/1986 | Sahota |
| 4,737,153 A | 4/1988 | Shimamura et al. |
| 4,748,982 A | 6/1988 | Horzewski et al. |
| 4,892,519 A | 1/1990 | Songer et al. |

(Continued)

FOREIGN PATENT DOCUMENTS

| CN | 101400400 A | 4/2009 |
| CN | 102802698 A | 11/2012 |

(Continued)

OTHER PUBLICATIONS

"Cook Medical Flexor Technology". Published 2013. Accessed May 5, 2019. <https://www.cookmedical.com/data/resources/PI-BM-KCF-EN-201302_WEB.pdf> (Year: 2013).*

(Continued)

*Primary Examiner* — Kami A Bosworth
(74) *Attorney, Agent, or Firm* — Shay Glenn LLP

(57) ABSTRACT

A balloon catheter assembly is provided with an outer catheter, an inner catheter, an outer adapter and a balloon, and is configured such that the balloon resides entirely within a predetermined volume having an outer diameter substantially equal to or less than the outside diameter of the distal end of the outer catheter when the balloon is in a deflated configuration. Methods of using and steering the catheter assemblies are also provided.

12 Claims, 7 Drawing Sheets

(56) References Cited

U.S. PATENT DOCUMENTS

| | | |
|---|---|---|
| 4,896,669 A | 1/1990 | Bhate et al. |
| 4,909,252 A | 3/1990 | Goldberger |
| 4,944,745 A | 7/1990 | Sogard et al. |
| 4,976,690 A | 12/1990 | Solar et al. |
| 4,990,143 A | 2/1991 | Sheridan |
| 5,000,734 A | 3/1991 | Boussignac et al. |
| 5,040,548 A | 8/1991 | Yock |
| 5,047,045 A | 9/1991 | Arney et al. |
| 5,078,685 A | 1/1992 | Colliver |
| 5,090,958 A | 2/1992 | Sahota |
| 5,100,386 A | 3/1992 | Inoue |
| 5,137,513 A | 8/1992 | Mcinnes et al. |
| 5,156,594 A | 10/1992 | Keith et al. |
| 5,217,434 A | 6/1993 | Arney |
| 5,279,562 A | 1/1994 | Sirhan et al. |
| 5,334,154 A | 8/1994 | Samson et al. |
| 5,342,386 A * | 8/1994 | Trotta .................. A61L 29/049 604/523 |
| 5,356,388 A | 10/1994 | Sepetka et al. |
| 5,370,655 A * | 12/1994 | Burns ................. A61M 25/104 604/913 |
| 5,423,754 A * | 6/1995 | Cornelius ........... A61M 25/104 604/103 |
| 5,423,829 A | 6/1995 | Pham et al. |
| 5,429,605 A | 7/1995 | Richling |
| 5,454,795 A | 10/1995 | Samson |
| 5,470,314 A | 11/1995 | Walinsky |
| 5,484,409 A * | 1/1996 | Atkinson .......... A61M 25/0023 604/103.03 |
| 5,498,251 A | 3/1996 | Dalton |
| 5,501,667 A | 3/1996 | Verduin |
| 5,509,910 A | 4/1996 | Lunn |
| 5,556,383 A | 9/1996 | Wang et al. |
| 5,582,619 A | 12/1996 | Ken |
| 5,588,442 A | 12/1996 | Scovil et al. |
| 5,599,326 A | 2/1997 | Carter |
| 5,624,449 A | 4/1997 | Pham et al. |
| 5,643,254 A | 7/1997 | Scheldrup et al. |
| 5,647,198 A | 7/1997 | Mihailovic |
| 5,649,949 A | 7/1997 | Wallace et al. |
| 5,669,905 A | 9/1997 | Scheldrup et al. |
| 5,674,198 A | 10/1997 | Leone |
| 5,690,666 A | 11/1997 | Berenstein et al. |
| 5,690,667 A | 11/1997 | Gia |
| 5,718,711 A | 2/1998 | Berenstein et al. |
| 5,722,424 A | 3/1998 | Engelson |
| 5,749,837 A | 5/1998 | Palermo et al. |
| 5,766,192 A | 6/1998 | Zacca |
| 5,769,830 A | 6/1998 | Parker |
| 5,792,300 A | 8/1998 | Inderbitzen et al. |
| 5,797,874 A | 8/1998 | Spears |
| 5,800,454 A | 9/1998 | Jacobsen et al. |
| 5,807,355 A | 9/1998 | Ramzipoor et al. |
| 5,830,182 A | 11/1998 | Wang et al. |
| 5,833,705 A | 11/1998 | Ken et al. |
| 5,843,032 A | 12/1998 | Kastenhofer |
| 5,843,050 A | 12/1998 | Jones et al. |
| 5,851,203 A | 12/1998 | Van Muiden |
| 5,853,418 A | 12/1998 | Ken et al. |
| 5,891,128 A | 4/1999 | Gia et al. |
| 5,911,717 A | 6/1999 | Jacobsen et al. |
| 5,951,539 A | 9/1999 | Nita et al. |
| 5,951,929 A | 9/1999 | Wilson |
| 5,984,878 A | 11/1999 | Engelson |
| 5,984,929 A | 11/1999 | Bashiri et al. |
| 6,013,084 A | 1/2000 | Ken et al. |
| 6,014,919 A | 1/2000 | Jacobsen et al. |
| 6,019,757 A | 2/2000 | Scheldrup |
| 6,022,340 A | 2/2000 | Sepetka et al. |
| 6,036,382 A | 3/2000 | Lange et al. |
| 6,036,670 A | 3/2000 | Wijeratne et al. |
| 6,036,682 A | 3/2000 | Lange et al. |
| 6,066,157 A | 5/2000 | Barbere |
| 6,066,667 A | 5/2000 | Ashbrook |
| 6,071,286 A | 6/2000 | Mawad |
| 6,090,099 A | 7/2000 | Samson et al. |
| 6,123,714 A | 9/2000 | Gia et al. |
| 6,156,061 A | 12/2000 | Wallace et al. |
| 6,165,163 A | 12/2000 | Chien et al. |
| 6,187,027 B1 | 2/2001 | Mariant et al. |
| 6,190,358 B1 | 2/2001 | Fitzmaurice et al. |
| 6,203,547 B1 | 3/2001 | Nguyen et al. |
| 6,258,080 B1 | 7/2001 | Samson |
| 6,270,495 B1 | 8/2001 | Palermo |
| 6,280,457 B1 | 8/2001 | Wallace et al. |
| 6,287,301 B1 | 9/2001 | Thompson et al. |
| 6,319,228 B1 | 11/2001 | Kastenhofer |
| 6,344,041 B1 | 2/2002 | Kupiecki et al. |
| 6,397,850 B1 | 6/2002 | Scheldrup et al. |
| 6,423,085 B1 | 7/2002 | Murayama et al. |
| 6,428,489 B1 | 8/2002 | Jacobsen et al. |
| 6,440,088 B1 | 8/2002 | Jacobsen et al. |
| 6,468,266 B1 | 10/2002 | Bashiri et al. |
| 6,471,673 B1 | 10/2002 | Kastenhofer |
| 6,508,804 B2 | 1/2003 | Sarge et al. |
| 6,553,880 B2 | 4/2003 | Jacobsen et al. |
| 6,575,959 B1 | 6/2003 | Sarge et al. |
| 6,579,246 B2 | 6/2003 | Jacobsen et al. |
| 6,635,069 B1 | 10/2003 | Teoh et al. |
| 6,638,245 B2 | 10/2003 | Miller et al. |
| 6,652,508 B2 | 11/2003 | Griffin et al. |
| 6,656,550 B1 | 12/2003 | Zamore |
| 6,702,782 B2 | 3/2004 | Miller et al. |
| 6,702,802 B1 | 3/2004 | Hancock et al. |
| 6,706,025 B2 | 3/2004 | Engelson et al. |
| 6,766,720 B1 | 7/2004 | Jacobsen et al. |
| 6,780,181 B2 | 8/2004 | Kroll et al. |
| 6,835,189 B2 | 12/2004 | Musbach et al. |
| 6,860,893 B2 | 3/2005 | Wallace et al. |
| 6,860,899 B1 | 3/2005 | Rivelli |
| 6,878,151 B2 | 4/2005 | Carrison et al. |
| 6,921,410 B2 | 7/2005 | Porter |
| 6,936,055 B1 | 8/2005 | Ken et al. |
| 6,997,937 B2 | 2/2006 | Jacobsen et al. |
| 7,004,962 B2 | 2/2006 | Stinson |
| 7,037,330 B1 | 5/2006 | Rivelli et al. |
| 7,060,083 B2 | 6/2006 | Gerberding |
| 7,070,607 B2 | 7/2006 | Murayama et al. |
| 7,144,407 B1 | 12/2006 | Lasersohn |
| 7,153,323 B1 | 12/2006 | Teoh et al. |
| 7,166,122 B2 | 1/2007 | Aganon et al. |
| 7,294,137 B2 | 11/2007 | Rivelli et al. |
| 7,332,689 B2 | 2/2008 | Mertens et al. |
| 7,412,285 B2 | 8/2008 | Schroeppel et al. |
| 7,468,070 B2 | 12/2008 | Henry et al. |
| 7,481,800 B2 | 1/2009 | Jacques |
| 7,621,904 B2 | 11/2009 | McFerran et al. |
| 7,645,259 B2 | 1/2010 | Goldman |
| 7,654,979 B2 | 2/2010 | Simpson |
| 7,742,811 B2 | 6/2010 | Schroeppel et al. |
| 7,780,626 B2 | 8/2010 | Wu et al. |
| 7,942,847 B2 | 5/2011 | Stupecky et al. |
| 7,998,165 B2 | 8/2011 | Huffmaster |
| 8,066,667 B2 | 11/2011 | Hayman et al. |
| 8,092,508 B2 | 1/2012 | Leynov et al. |
| 8,202,292 B2 | 6/2012 | Kellett |
| 8,206,373 B2 | 6/2012 | Zhou |
| 8,348,890 B2 | 1/2013 | Gerrans et al. |
| 8,961,550 B2 | 2/2015 | Lenker et al. |
| 9,174,020 B2 | 11/2015 | Allen et al. |
| 9,205,226 B2 | 12/2015 | Allen et al. |
| 9,427,550 B2 | 8/2016 | Dakin et al. |
| 9,550,046 B1 | 1/2017 | Allen |
| 9,555,165 B2 | 1/2017 | Phan |
| 2001/0041862 A1 | 11/2001 | Glickman |
| 2002/0032457 A1 | 3/2002 | Sirhan et al. |
| 2003/0050600 A1 | 3/2003 | Ressemann et al. |
| 2003/0114878 A1 | 6/2003 | Diederich et al. |
| 2003/0191435 A1 | 10/2003 | Shkolnik |
| 2003/0199914 A1 | 10/2003 | Diaz |
| 2005/0131453 A1 | 6/2005 | Parodi |
| 2005/0267407 A1 | 12/2005 | Goldman |
| 2006/0106413 A1 | 5/2006 | Bence et al. |
| 2006/0276886 A1 | 12/2006 | George et al. |

(56) References Cited

U.S. PATENT DOCUMENTS

| | | | |
|---|---|---|---|
| 2007/0088380 A1 | 4/2007 | Hirszowicz et al. | |
| 2007/0137651 A1 | 6/2007 | Glassenberg et al. | |
| 2007/0149927 A1 | 6/2007 | Itou et al. | |
| 2008/0045908 A1 | 2/2008 | Gould et al. | |
| 2008/0208118 A1 | 8/2008 | Goldman | |
| 2008/0262470 A1 | 10/2008 | Lee et al. | |
| 2009/0131831 A1 | 5/2009 | Wright et al. | |
| 2009/0156999 A1 | 6/2009 | Adams et al. | |
| 2009/0177183 A1 | 7/2009 | Pinkernell et al. | |
| 2010/0030200 A1 | 2/2010 | Strauss et al. | |
| 2010/0113939 A1 | 5/2010 | Mashimo et al. | |
| 2010/0222637 A1 | 9/2010 | Kassab | |
| 2010/0249491 A1* | 9/2010 | Farnan | A61M 1/3653 600/16 |
| 2012/0203173 A1 | 8/2012 | Davies et al. | |
| 2012/0253447 A1 | 10/2012 | Hayasaka et al. | |
| 2013/0131610 A1* | 5/2013 | Dewaele | A61B 5/0215 604/264 |
| 2014/0163421 A1 | 6/2014 | Van Hoven | |
| 2014/0371709 A1* | 12/2014 | Allen | A61M 25/10 604/503 |
| 2014/0371718 A1 | 12/2014 | Alvarez et al. | |
| 2015/0351729 A1 | 12/2015 | Chin et al. | |
| 2016/0008585 A1 | 1/2016 | Tano | |
| 2016/0096002 A1 | 4/2016 | Di Caprio et al. | |
| 2016/0101261 A1 | 4/2016 | Kugler et al. | |
| 2016/0158439 A1 | 6/2016 | Allen | |
| 2016/0213893 A1 | 7/2016 | Franklin | |
| 2016/0310148 A1 | 10/2016 | Allen | |
| 2017/0049495 A1 | 2/2017 | Yu et al. | |
| 2017/0095646 A1 | 4/2017 | Norman et al. | |
| 2019/0329007 A1 | 10/2019 | Allen et al. | |

FOREIGN PATENT DOCUMENTS

| | | |
|---|---|---|
| CN | 102805893 A | 12/2012 |
| EP | 1131126 B1 | 8/2004 |
| EP | 2389968 A2 | 11/2011 |
| JP | H05-15604 A | 1/1993 |
| JP | H07-213617 A | 8/1995 |
| JP | 2003500121 A | 1/2003 |
| JP | 2005511108 A | 4/2005 |
| JP | 2006511271 A | 4/2006 |
| JP | 2007319468 A | 12/2007 |
| WO | WO 89/08471 A1 | 9/1989 |
| WO | WO 2004/107965 A2 | 12/2004 |
| WO | WO2012/009486 A2 | 1/2012 |
| WO | WO2012/099979 A1 | 7/2012 |
| WO | WO2014/008489 A1 | 1/2014 |

OTHER PUBLICATIONS

Allen; U.S. Appl. No. 15/844,389 entitled "Devices and methods for low pressure tumor embolization," filed Dec. 15, 2017.

Cliffton et al.; Technique for visualization and perfusion of bronchial arteries: suggested clinical and diagnostic applications; Cancer; 16; pp. 444-452; Apr. 1963.

Rousselot et al.; Selective concentration of anticancer drugs in the liver: Hepatic-artery infusion and induced hepatic outflow block; JAMA; 191(9); pp. 707-710; Mar. 1965.

Halstead et al.; U.S. Appl. No. 16/004,247 entitled "High torque catheter and methods of manufacture," filed Jun. 8, 2018.

Halstead et al.; U.S. Appl. No. 16/047,922 entitled "Shaped catheter tip for tracking over a guidewire through turns in the vasculature," filed Jul. 27, 2018.

Allen U.S. Appl. No. 16/196,398 entitled "Device and methods for transvascular tumor embolization," filed Nov. 20, 2018.

Angiodynamics; Soft-vu angiographic catheters; 2 pages; retrieved from the internet (http://www.angiodynamics.com/products/soft-vu) on Aug. 17, 2018.

BMI ESPICOM Pharmaceutical and Medical Device News; Business Monitor Online: Vascular solutions expands complex intervention offerings with turnpike LP catheter; newsleter; 2pages; retrieved from the internet (https://dialog.proquest.com/professional/docview/1753127273?accountid=157282) on Apr. 18, 2018 (Abstract Only).

Matsuda et al.; Electrospinning fabrication of high-trackable catheter tip with gradually graded or gradient flexibility; J. Biomed. Mater. Res. B Appl. Biomater.; 1(35); pp. 35-41 doi: 10.1002/jbm.b.31061; (Abstract Only); Oct. 2008.

Nordson Medical; Extruded tubing technical information; 7 pages; retrieved from the internet (https://www.nordsonmedical.com/Components-and-Technologies/Medical-Tubing/Extruded-Tubing/Technical-Information/) on Aug. 17, 2018.

Vante Plasticweld Systems; Bonds and welds; 13 pages; retrieved from the internet (https://cathetertipping.com/home/our-products/bonding/) on Aug. 17, 2018.

Worldwide Videotex; Angiodynamics PCTA balloon catheter gets FDA market clearance; Biotech Equipment Update 5.9: N/A. Worldwide Videotex; Sep. 1, 1997; 2 pages; retrieved from the internet (https://dialog.proquest.com/professional/docview/680080033?accountid=157282) on Apr. 18, 2018 (Abstract Only).

Zeus; FluoroPEELZ peelable heat shrink; 9 pages; retrieved from the internet (https://www.zeusinc.com/products/heat-shrinkable-tubing/fluoropeelz-peelable-heat-shrink) on Aug. 17, 2018.

Halstead et al.; U.S. Appl. No. 16/545,519 entitled "Balloon catheters and methods of manufacture and use," filed Aug. 20, 2019.

* cited by examiner

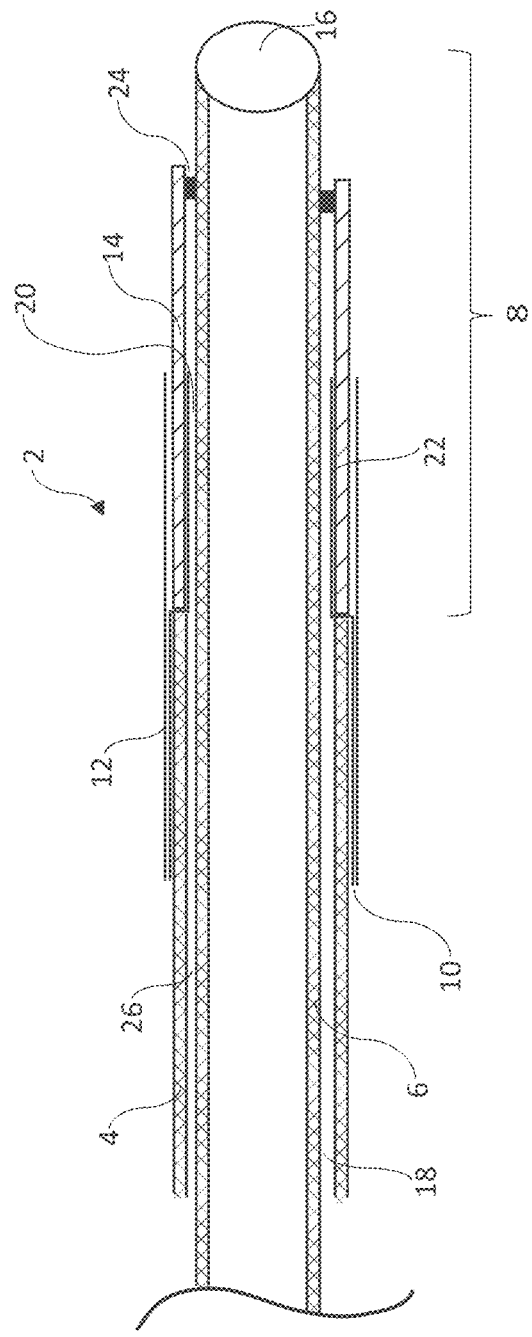
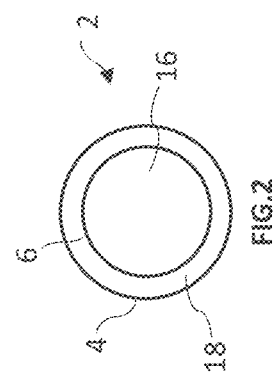
FIG. 1
FIG. 2

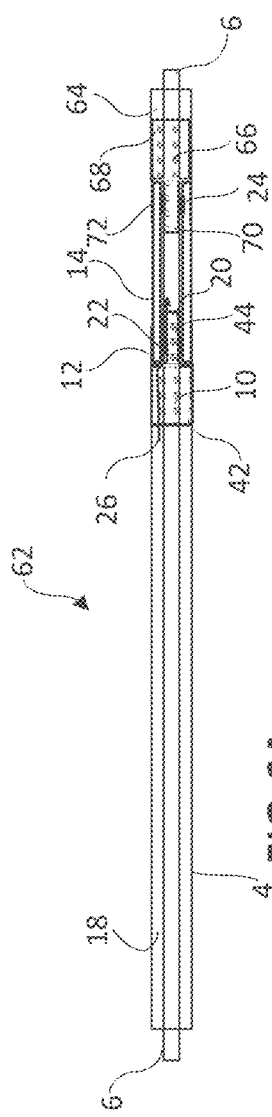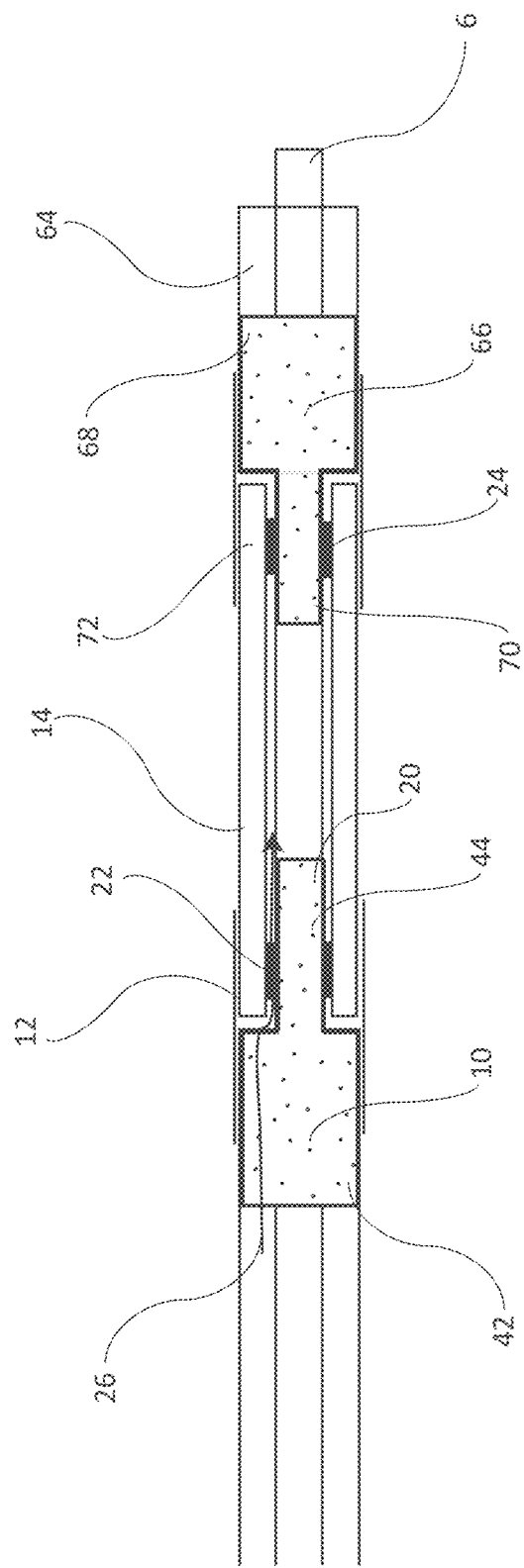

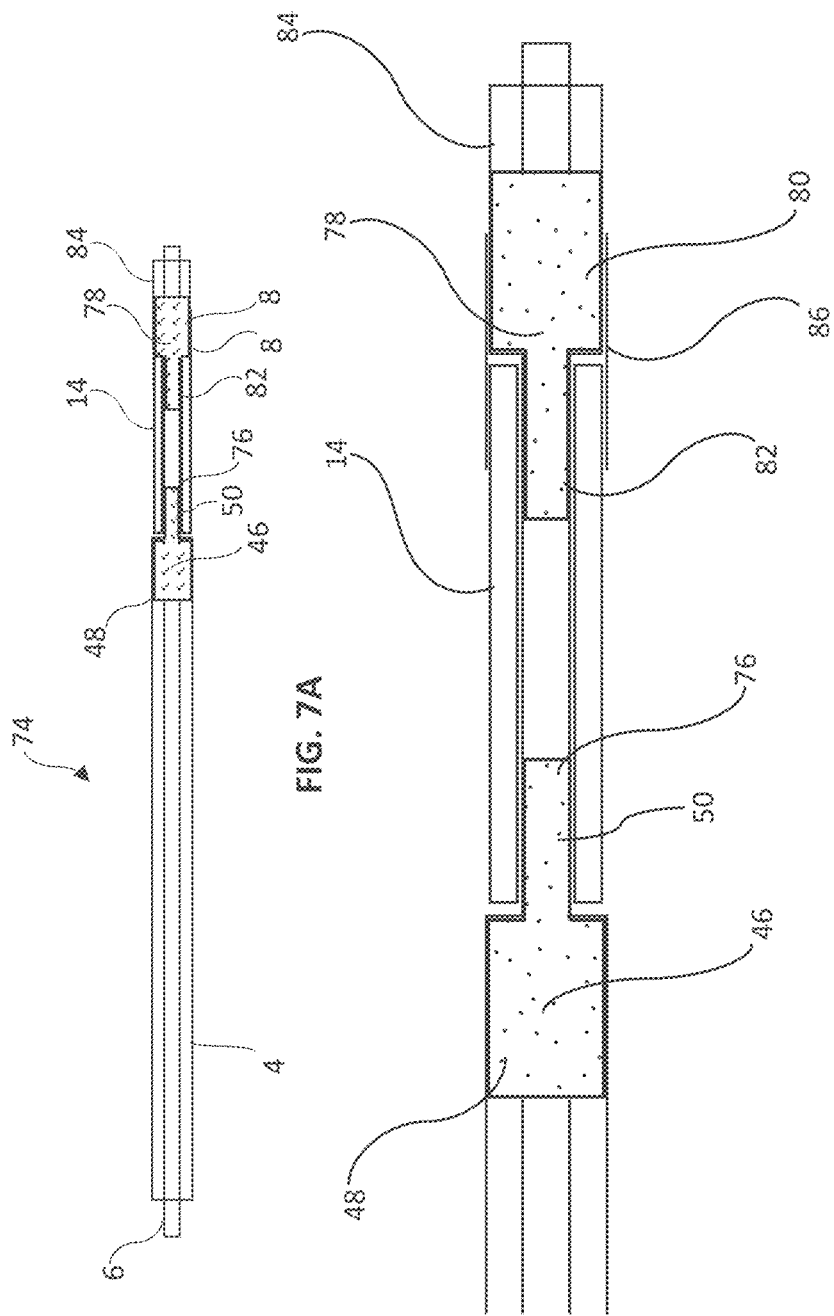

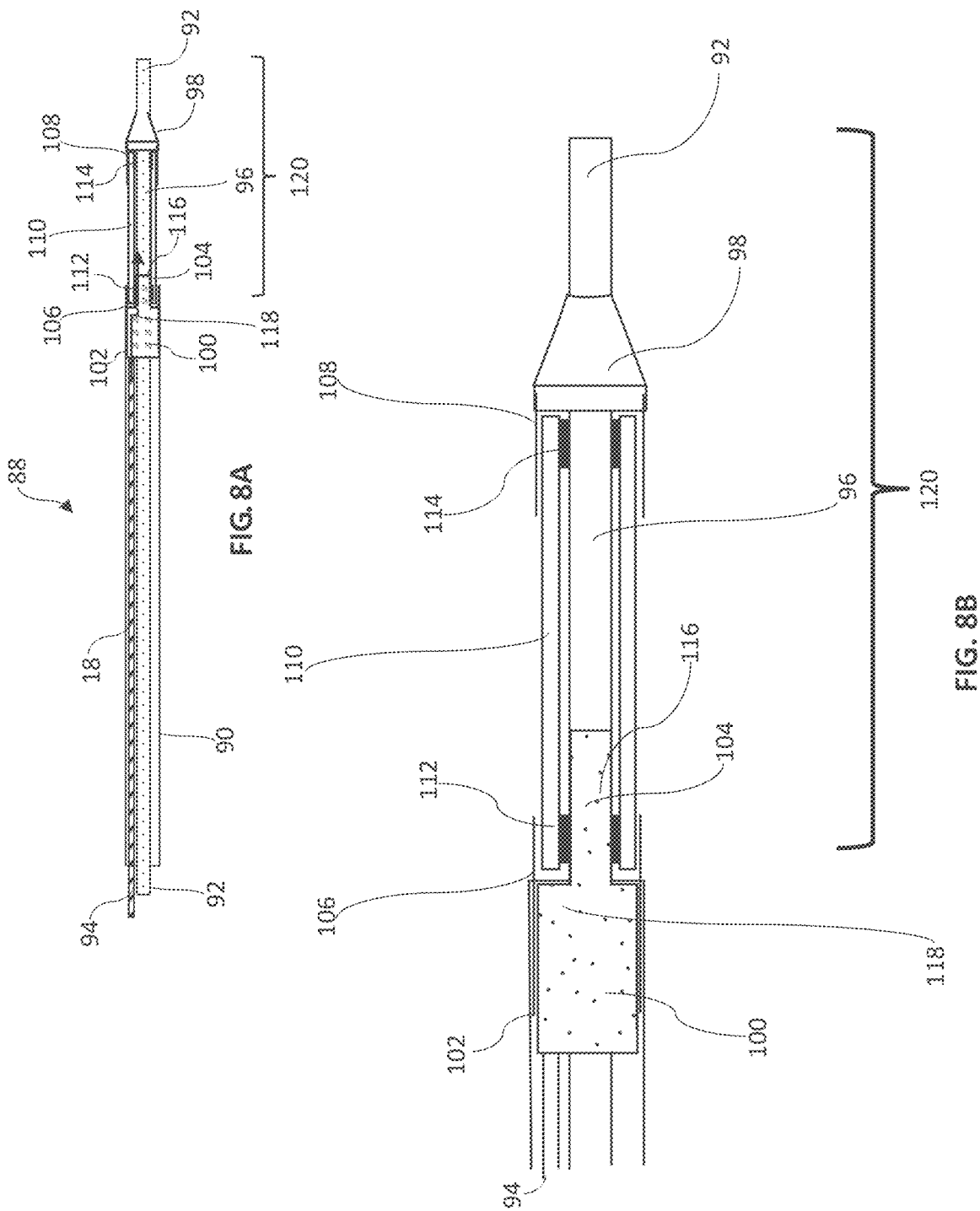

OCCLUSION BALLOON CATHETER AND METHODS OF FABRICATION AND USE

CROSS REFERENCE TO RELATED APPLICATIONS

This application is a continuation of U.S. application Ser. No. 15/044,864 filed Feb. 16, 2016. This application is related to U.S. application Ser. No. 14/273,445, entitled "Device and Methods for Transvascular Tumor Embolization with Integrated Flow Regulation", filed May 8, 2014, now U.S. Pat. No. 9,205,226.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

This application relates generally to medical methods and devices. More specifically, the present disclosure relates to devices and methods to affix a balloon below the surface of a catheter and to achieve a low profile for entering small vasculature.

BACKGROUND

Catheters are commonly used in medicine for delivery of fluids, therapeutics and implants as well as in sampling tissues and bodily fluids. Catheters can be constructed with balloons or other tools to dilate tissue, block fluid flow or isolate segments of the anatomy. A relatively common use for a catheter is the delivery of drugs to a target tissue using blood vessels as a means of access. When a balloon is used, the vascular compartment distal to the balloon is isolated from the vascular compartment proximal to the balloon and perfusion of diagnostic, therapeutic or embolic agents is localized and concentrated. Transvascular catheters, especially in the peripheral blood circulation, need to have a small axial diameter to allow access into small vessels.

One common use for a microcatheter is the delivery of embolic agents and anticancer drugs to a tumor.

According to the NIH, 30,640 people were diagnosed with primary liver cancer (hepatocellular carcinoma, HCC) and 142,820 people were diagnosed with colorectal cancer in the US in 2013. Seventy five percent of these will metastasize to the liver. Liver resection and transplant are the only curative means; however, only small numbers of patients are eligible. Systemic Chemotherapy for primary and metastatic tumors in the liver is ineffective, having a response rate of about 20% and a survival benefit of 10.7 months vs. 7.9 months over symptomatic care.

Trans-Arterial Embolization therapy is the transvascular injection of drug and/or embolic agents directly into, or in the vicinity of, the tumor vasculature using a microcatheter. Embolization therapy causes a shutdown of blood flow and, when drug or radioactivity is present, simultaneous release of high concentrations of drug or radioactivity. The technique is also noted for its very low level of toxicity. Chemoembolization was established as a standard of care for intermediate stage hepatocellular carcinoma in 2006.

Numerous studies have demonstrated transarterial embolization to be effective on a number of primary cancers and to have better performance than chemotherapy for both HCC and metastatic colorectal cancers in the liver; however, studies show inconsistent outcomes with reported tumor responses from 15% to 85%. Although anatomical and individual differences are clearly of significance in between-patient variation, clinical studies, each of which include a range of patients, show very different outcomes, indicating that procedural standardization is needed.

The present state-of-the-art embolization therapy for tumors in the liver relies on high volume "forward flow" from the hepatic artery that is flowing at about 6 ml/sec to deliver embolization agents into the tumor. As embolization progresses, the distal capillaries become occluded and the tumor can no longer accept this high flow rate, even though the tumor is only partially filled with embolic agents. Tumor embolization using high volume flow from the unrestricted hepatic artery causes: (1) rapid embolization of the distal portions of tumor capillaries, (2) rapid onset of high intra-tumor pressure, (3) reflux of blood and embolic agents from the tumor, (4) increased non-target flow into hepatoenteric arteries, and (5) poor filling and distribution of embolic agents in the tumor. This situation results in an uncontrollable number of particles or other embolic agents entering the tumor and high procedural variability.

Although standardization to an optimal protocol should improve reproducibility and overall outcomes, the procedure is presently without optimization or standardization. The current delivery catheters are unable to control many of the above mentioned variables, making standardization unlikely. There is a need for a delivery system that enables a measurable clinical endpoint, a known quantity of embolic agent delivered, and elimination of non-target embolization. This is a required first step if standardization is to be achieved.

As a requirement, a delivery catheter that would solve the aforementioned problems, must have a small radial diameter to allow access into small vessels that are typically in the vicinity of the tumor. Presently, balloons are bonded to the external surface of a catheter and necessarily increase its diameter. It would be a significant advantage to construct a balloon catheter whereby a balloon was positioned below the surface of the catheter when in its constrained configuration and return thereto following inflation and deflation. One method to accomplish this is to configure a circumferentially oriented pocket or pockets in a catheter whereby a balloon bonding surface is positioned below the surface of the catheter. The present disclosure is a device and method that achieves a low profile catheter by positioning the balloon bonding surfaces below the surface of a drug delivery catheter.

U.S. patent application Ser. No. 10/128,977 describes a coaxial catheter whereby a balloon is bonded to an elongated outer tube to prevent the balloon from telescopingly buckling when the balloon is being pushed across a narrow passage. U.S. Pat. No. 6,066,157 describes a coaxial coronary angioplasty catheter whereby an anchor joint is configured to allow distal movement of the inner tube and to prevent proximal movement. U.S. Pat. No. 5,647,198 describes a catheter with a pair of spaced apart balloons that define an intra-balloon space. A lumen passes through the catheter and exits within the intra-balloon space allowing injection of drugs, emulsions, fluids and fluid/solid mixtures. A perfusion lumen or bypass extends from a location proximal to the proximal balloon and to the distal tip to allow shunting of blood past the inflated balloons. U.S. Pat. No. 5,674,198 describes a two balloon catheter that is designed for treating a solid tumor. The balloons are positioned to isolate the blood flow into the tumor and allow injection of a vaso-occlusive collagen material to block the tumor blood supply. Clifton et al. (1963) *Cancer* 16:444-452 describes a two balloon catheter for the treatment of lung carcinoma. The four lumen catheter includes a lumen for independent injection in the space between the balloons. Rousselot et al. (1965) *JAMA* 191:707-710 describes a balloon catheter device for delivering anticancer drugs into the liver. See also U.S. Pat. Nos. 6,780,181; 6,835,189; 7,144,407; 7,412,285; 7,481,800; 7,645,259; 7,742,811; U.S. App. No. 2001/008451; U.S. App. No. 2001/0041862; U.S. App. No. 2003/008726; U.S. App. No. 2003/0114878; U.S. App. No. 2005/0267407; U.S. App. No. 2007/0137651; U.S. App. No. 2008/0208118; U.S. App. No. 2009/0182227 and U.S. App. No. 2010/0114021.

What is needed and is not provided in the prior art is a means of positioning of balloon bonding surfaces and attachment of a balloon below the surface of a catheter body and allow a low profile catheter that is useful in providing therapy within small blood vessels.

SUMMARY OF DISCLOSURE

According to aspects of the present disclosure, devices are provided for attachment of a balloon or other vascular occlusion device or tool to a catheter whereby the device bonding surfaces are positioned below the surface of the outer diameter of a catheter body. Such catheters are intended for many medical purposes, but the embodiments described herein are focused on microcatheters intended to perform medical procedures in small blood vessels within the body. Such a catheter can access the vascular system percutaneously from any convenient artery or vein including, but not limited to, the femoral artery, carotid artery or jugular vein.

In some embodiments of the present disclosure a device comprises an outer catheter, an inner coaxial catheter, an outer adapter, a support sheath and a balloon. The inflatable balloon has an inner surface that at least partially defines an interior volume. The balloon also has a proximal surface and a distal surface and a channel that extends longitudinally through the balloon, said channel is configured to provide fluid communication between the proximal surface of the balloon and the distal surface of the balloon. The outer catheter has a proximal end, a distal end and a lumen that extends therethrough. The inner catheter is a smaller diameter than the outer catheter and has a proximal end, a distal end and a lumen extending therethrough. The inner catheter is positioned inside the outer catheter, thereby forming an annular space between the inner and outer catheter, said annular space is in fluid communication with the inner volume of the balloon and provides a lumen for balloon inflation and deflation. The inner catheter extends distally for some distance beyond the distal end of the outer catheter, providing a reduced diameter whereby a balloon or other accessory can be circumferentially disposed at a level that is below the outer catheter. At its distal end, the balloon can be bonded to the extension of the inner catheter. The proximal end of the balloon is attachable to the distal end of the outer catheter using the adapter and support sheath of the present disclosure and allows the balloon to be bonded below the surface of the outer diameter of the outer catheter with a channel extending from the distal end of the catheter assembly to the inner volume of a balloon and, if needed, close abutment of the proximal end of the balloon to the distal end of the outer catheter. In this instance, the proximal end of the adapter is larger in diameter than the distal aspect and is attached to outer distal end of the outer catheter, typically in a manner that positions the proximal adapter below the surface of the distal outer catheter. The distal aspect of the adapter has a smaller diameter than the proximal aspect, whereby the outer surface of the distal aspect of the adapter is positioned below the surface of the outer catheter and a balloon can be bonded to the outer surface of the distal aspect of the adapter, thereby positioning the balloon bonding surface below the outer catheter surface. The proximal portion of a support sheath can be attached circumferentially to the outer surface of the distal outer catheter, typically in a manner that positions the sheath below the surface of the distal outer catheter and the distal portion of the sheath is positioned over the proximal end of the balloon. One advantage of the sheath of the present disclosure is to hold the proximal balloon to the distal adapter and thereby strengthening the balloon attachment. Advantages of the device of the present disclosure include a balloon with at least one bond below the outer surface of an outer catheter, providing a low profile, a strong bonding of the balloon to the catheter assembly and rapid inflation and deflation of a balloon, even with viscous solutions such as radiopaque contrast media.

In some embodiments of the present disclosure, the device comprises an outer catheter, an inner coaxial catheter, a sheath, an inner adapter and a balloon. The outer catheter has a proximal end, a distal end and a lumen that extends therethrough. The inner catheter is a smaller diameter than the outer catheter and has a proximal end, a distal end and a lumen extending therethrough. An inflatable balloon has an inner surface that at least partially defines an interior volume. The balloon also has a proximal surface and a distal surface and a channel that extends longitudinally through the balloon, said channel is configured to provide fluid communication between the proximal surface of the balloon and the distal surface of the balloon. The inner catheter is positioned inside the outer catheter, thereby forming an annular space between the inner and outer catheter, said annular space is in fluid communication with the inner volume of the balloon and provides a lumen for balloon inflation and deflation. The inner catheter extends distally for some distance beyond the distal end of the outer catheter, providing a reduced diameter whereby a balloon or other accessory can be circumferentially disposed at a level that is below the outer catheter. At its distal end, the balloon can be bonded to the extension of the inner catheter. The balloon is attachable to the distal end of the outer catheter using the an inner adapter and sheath of the present disclosure which allow the distal balloon bond to be positioned below the surface of the outer diameter of the outer catheter and, if needed, close abutment of the proximal end of the balloon to the distal end of the outer catheter. In this instance, the proximal end of the adapter is attached to the inner lumenal surface of the distal end of the outer catheter. The proximal portion of the support sheath is attached to the outer surface of the distal outer catheter, typically in a manner that positions the sheath below the surface of the distal outer catheter and the distal portion of the sheath is positioned over the proximal end of the balloon, whereby it may or may not be affixed. Advantages of the adapter are to provide a bonding surface for a balloon that is below the surface of a catheter assembly and provide an annular inflation channel which allows the balloon to inflate and deflate rapidly, even with viscous fluids such as contrast media. An advantage of the support sheath of the present disclosure is to hold the proximal balloon to the adapter and thereby strengthening the balloon attachment.

In some embodiments of the present disclosure, a device comprises a two lumen catheter, a support sheath, an outer adapter and a balloon. The inflatable balloon has an inner surface that at least partially defines an interior volume. The balloon also has a proximal surface and a distal surface and a channel that extends longitudinally through the balloon, said channel is configured to provide fluid communication between the proximal surface of the balloon and the distal surface of the balloon. The two lumen catheter has a proximal end, a distal end and two lumens, a first injection lumen that is in fluid communication with the distal end of the catheter and provides a channel to deliver therapeutic agents to a target tissue or aspirate fluids for analysis and a second lumen that is in fluid communication with the interior surface of the balloon and provides for inflation and deflation. The first injection lumen typically extends for some distance distally beyond the end of the inflation lumen and provides a reduced diameter for circumferential attachment of a balloon or other accessory. The balloon is attachable to the distal end of the catheter using the adapter and sheath of the present disclosure in a manner that positions the balloon bonding surfaces and, if desired, the balloon outer diameter, below the surface of the outer diameter of the outer catheter and, if needed, close abutment of the proximal end of the balloon to the distal end of the catheter. Although it is typically desirable that the balloon outer diameter be positioned below the outer diameter of the catheter, in some instances it may be desirable for the balloon to extend circumferentially outward beyond the outer diameter of the catheter. In this instance, the proximal end of the adapter is larger in diameter than the distal aspect, whereby the inner surface of the balloon is bonded to the outer surface of the distal aspect of the adapter and the inner surface of the proximal aspect of the adapter is attached to distal end of the outer catheter, typically in a manner that positions the proximal adapter substantially below the surface of the distal outer catheter. The proximal portion of a support sheath is attached to the outer surface of the distal outer catheter, typically in a manner that positions the support sheath substantially below the surface of the distal outer catheter and the distal portion of the sheath is positioned over the proximal end of the balloon and may, if desired, be bonded thereto. The distal end of the balloon can then be affixed to the extension of the first lumen whereby the bonding surfaces of the balloon are positioned below the surface of the largest diameter of the catheter assembly. One advantage of the sheath of the present disclosure is to hold the proximal balloon to the distal adapter and thereby strengthening the balloon attachment and compressing the bond joint to minimize size. Advantages of the adapter of the present disclosure are to position the balloon bonding areas below the surface of a catheter assembly and to provide a substantially circumferential balloon inflation area that can allow rapid and substantially symmetrical inflation and deflation, even with viscous solutions such as radiopaque contrast media.

In some embodiments of the present disclosure a nose piece, nose cone, marker band or other similar structure is positioned circumferentially about an extension of the inner catheter or injection lumen and distal to the distal end of the balloon inflation lumen, whereby the proximal end the balloon is bonded according to the present disclosure below the surface of the catheter and the distal end of the balloon can be bonded directly to the distal extension or to the nose piece using the device of the present disclosure, provided that all balloon bonding surfaces are below the outer diameter of the catheter assembly. In this instance, a pocket is formed between the distal catheter and the proximal end of the nose piece.

In some embodiments of the present disclosure a device comprises a first outer catheter, a second outer catheter, an inner coaxial catheter, at least one outer or inner adapter, at least one support sheath and a balloon. The inner catheter is positioned inside the outer catheter, thereby forming an annular space between the inner and outer catheter, said annular space is in fluid communication with the inner volume of the balloon and provides a lumen for balloon inflation and deflation. The inner catheter extends distally for some distance beyond the distal end of the first outer catheter, providing a reduced diameter, whereby a balloon or other accessory can be circumferentially disposed at a level that is below the outer catheter. The second outer catheter is configured such that it can be circumferentially oriented about the distal extension of the inner catheter at some distance from the distal end of the first outer catheter to form a pocket between the distal end of the first outer catheter and the second outer catheter. For the purpose of this embodiment, the first outer catheter and the second outer catheter are of the same diameter, however, the first outer catheter and the second outer catheter need not have the same diameter. A balloon is oriented circumferentially about the inner catheter at a position that is distal to the first outer catheter and proximal to the second outer catheter and within a pocket formed therebetween. The proximal end the balloon is bonded according to the present disclosure below the surface of the first outer catheter and the distal end of the balloon can be bonded directly to the distal extension or to the second outer catheter using the device of the present disclosure, provided that all balloon bonding surfaces are below the outer diameter of the catheter assembly.

In some embodiments of the present disclosure an adapter is positioned at the proximal end of the balloon, the distal end of the balloon, or both proximal and distal ends of the balloon or an adapter is not present at either the proximal or distal ends of the balloon with the requirement that there is at least one adapter or one sheath at each balloon bonding location. In this instance, when an adapter in not present, the outer surface of the balloon is bonded to the inner surface of the sheath.

In some embodiments a sheath is positioned at the proximal end of the balloon, the distal end of the balloon, or both proximal and distal ends of the balloon or a sheath is not present at either the proximal or distal end of the balloon with the requirement that there is at least one adapter or sheath at each bonding location. In this instance, when an adapter in not present, the outer surface of the balloon is bonded to the inner surface of the sheath.

In some embodiments the sheath is positioned on the distal and/or proximal balloon and does not extend over the outer catheter and/or nose piece.

In some embodiments the sheath is replaced by a thread, clamp, band or other circumferential restraining device that is tightly wrapped about the balloon segment that is over the adapter.

In some embodiments, a balloon catheter assembly is provided with an outer catheter, an inner catheter, an outer adapter, a balloon and a support sheath. The outer catheter has a proximal end and a distal end, and the distal end has a wall thickness. The outer catheter comprises at least two layers including a reinforcing layer and a base layer which may be less rigid. The inner catheter is located coaxially within a lumen of the outer catheter, and the inner catheter has an injection lumen extending therethrough. The inner and outer catheters form an inflation lumen therebetween. The outer adapter has a proximal end and a distal end. The proximal end is sized to fit over an outside diameter of the distal end of the outer catheter and configured to be affixed thereto. The distal end of the outer adapter has a reduced outer diameter that is smaller than an outside diameter of the distal end of the outer catheter. The distal end of the outer adapter has an inside diameter that is larger than an outside diameter of the inner catheter, thereby forming a fluid channel therebetween that is in fluid communication with the inflation lumen. The outer adapter has a single layer and is formed of a material that is different from that of the outer catheter base layer. The outer adapter has a wall thickness that is no more than 15% of the wall thickness of the distal end of the outer catheter. The balloon has a proximal end with an inner surface affixed to the reduced outer diameter of the outer adapter, and the balloon has a distal end with an inner surface affixed to the outside diameter of the inner catheter. The balloon has an interior space that is in fluid communication with the fluid channel. The support sheath has a proximal end positioned over an outside diameter of the outer adapter and a distal end positioned over an outside diameter of the proximal end of the balloon. The support sheath is composed of a single layer, being formed of a material substantially the same as the material of the outer adapter, and having a wall thickness substantially the same as the wall thickness of the outer adapter. The balloon resides entirely within a predetermined volume having an outer diameter substantially equal to or less than the outside diameter of the distal end of the outer catheter when the balloon is in a deflated configuration. The balloon can be inflated by introducing a fluid through the inflation lumen and fluid channel into the interior space of the balloon. The balloon can then be deflated by removing the fluid from the interior space such that the balloon returns entirely within the predetermined volume.

In some of the above embodiments, the inner catheter has a distal end that extends distally beyond the distal end of the balloon. The balloon catheter assembly may further comprise a nosecone located on the distal end of inner catheter distal to the balloon, the nosecone having an outer diameter substantially equal to the outside diameter of the distal end of the outer catheter such that the balloon is recessed in a pocket formed between the nosecone and the outer catheter when the balloon is in the deflated configuration. The balloon catheter assembly may further comprise a proximal bond that affixes the inner surface of the proximal end of the balloon to the reduced outer diameter of the outer adapter, and a distal bond that affixes the inner surface of the distal end of the balloon to the outside diameter of the inner catheter. In some embodiments, both the proximal bond and the distal bond are located radially inward from the outside diameter of the distal end of the outer catheter. In some embodiments, both the proximal bond and the distal bond are located radially inward from an inside diameter of the distal end of the outer catheter. The inflation lumen may have a substantially annular cross-section. The outer catheter may comprise a base material and a different reinforcing material, and the outer adapter may be made of a plastic polymeric material. The reduced outer diameter portion of the outer adapter may have a wall thickness less than 0.01 mm. In some embodiments, the support sheath has a length that is at least as great as the outside diameter of the distal end of the outer catheter.

In some embodiments, methods of using a balloon catheter assembly are provided. The method may include providing a balloon catheter assembly having an outer catheter, an inner catheter, an outer adapter, a balloon and a support sheath. The outer catheter has a proximal end and a distal end, and the distal end has a wall thickness. The outer catheter has at least two layers including a reinforcing layer and a base layer which may be less rigid. The inner catheter is located coaxially within a lumen of the outer catheter, and the inner catheter has an injection lumen extending therethrough. The inner and outer catheters form an inflation lumen therebetween. The outer adapter has a proximal end and a distal end, the proximal end being sized to fit over an outside diameter of the distal end of the outer catheter and configured to be affixed thereto. The distal end of the outer adapter has a reduced outer diameter that is smaller than an outside diameter of the distal end of the outer catheter. The distal end of the outer adapter has an inside diameter that is larger than an outside diameter of the inner catheter, thereby forming a fluid channel therebetween that is in fluid communication with the inflation lumen. The outer adapter has a single layer and is formed of a material that is different from that of the outer catheter base layer. The outer adapter has a wall thickness that is no more than 15% of the wall thickness of the distal end of the outer catheter. The balloon has a proximal end with an inner surface affixed to the reduced outer diameter of the outer adapter, and has a distal end with an inner surface affixed to the outside diameter of the inner catheter. The balloon has an interior space that is in fluid communication with the fluid channel. The support sheath has a proximal end positioned over an outside diameter of the outer adapter and a distal end positioned over an outside diameter of the proximal end of the balloon. The support sheath is composed of a single layer, being formed of a material substantially the same as the material of the outer adapter, and has a wall thickness substantially the same as the wall thickness of the outer adapter.

The above methods may further include inserting a distal end of the balloon catheter assembly into a blood vessel of a body, and inflating the balloon by introducing a fluid through the inflation lumen and fluid channel into the interior space of the balloon to at least partially occlude blood flow in the blood vessel. The methods may also include injecting a substance into the blood vessel through the injection lumen, deflating the balloon by removing the fluid from the interior space of the balloon such that the balloon returns entirely within a predetermined volume having an outer diameter substantially equal to or less than the outside diameter of the distal end of the outer catheter, and withdrawing the distal end of the balloon catheter assembly from the blood vessel.

In some of the above methods, the inner catheter may have a distal end that extends distally beyond the distal end of the balloon. The balloon catheter assembly may further comprise a nosecone located on the distal end of inner catheter distal to the balloon, the nosecone having an outer diameter substantially equal to the outside diameter of the distal end of the outer catheter such that the balloon is recessed in a pocket formed between the nosecone and the outer catheter when the balloon is in the deflated configuration. The balloon catheter assembly may further comprise a proximal bond that affixes the inner surface of the proximal end of the balloon to the reduced outer diameter of the outer adapter, and a distal bond that affixes the inner surface of the distal end of the balloon to the outside diameter of the inner catheter. In some embodiments, the proximal bond and the distal bond are located radially inward from the outside diameter of the distal end of the outer catheter. In some embodiments, both the proximal bond and the distal bond are located radially inward from an inside diameter of the distal end of the outer catheter. The inflation lumen may have a substantially annular cross-section. The outer catheter may comprise a base material and a different reinforcing material, and the outer adapter may be made of a plastic polymeric material. In some embodiments, the reduced outer diameter portion of the outer adapter has a wall thickness less than 0.01 mm. The support sheath may have a length that is at least as great as the outside diameter of the distal end of the outer catheter.

In some embodiments, methods of steering a balloon catheter assembly are provided. The methods may include providing a balloon catheter assembly, the assembly comprising a catheter body having a proximal end and a distal tip portion, and a balloon affixed near the distal tip portion. The balloon may have an interior space that is in fluid communication with an inflation lumen extending from the balloon towards the proximal end of the catheter body. The methods may also include inserting the distal tip portion of the balloon catheter assembly into a blood vessel of a body, and inflating the balloon by introducing a fluid through the inflation lumen into the interior space of the balloon sufficient to laterally deflect the distal tip portion from a longitudinal axis of the catheter body. The catheter assembly is then advanced through the blood vessel in the direction of the deflected distal tip portion.

In some of the above methods, the advancing step comprises advancing the distal tip portion from the blood vessel into a branch vessel. The methods may also comprise extending a guidewire from the distal tip portion before the advancing step, and then advancing the distal tip over the extended guidewire. The methods may comprise locating a distal end of a guidewire within the catheter body at a point adjacent to the balloon before deflecting the distal tip portion. The methods may comprise rotating the catheter body axially after deflecting the distal tip portion such that the tip portion is pointed in a desired direction.

While aspects of the present disclosure will be described with particular reference to attachment of a balloon to a distal location on a catheter, the same principle can be applied to the attachment of any device that is positioned below the surface of a catheter.

BRIEF DESCRIPTION OF THE DRAWINGS

Novel features of the disclosure are set forth with particularity in the claims that follow. A better understanding of the features and advantages of the present disclosure will be obtained by reference to the following detailed description that sets forth illustrative embodiments, in which principles of the disclosure are utilized, and the accompanying drawings (which are not necessarily shown to scale) of which:

FIG. 1 is a longitudinal cross section of one embodiment of the present disclosure with balloon bonds below the surface of the outer catheter;

FIG. 2 is an axial cross section of a coaxial catheter;

FIG. 6A is a longitudinal cross section of an embodiment of the present disclosure including a second outer catheter;

FIG. 6B is an enlarged view of the distal end of the catheter shown in FIG. 6A;

FIG. 7A is a longitudinal cross section of an embodiment of the present disclosure including an inner adapter;

FIG. 7B is an enlarged view of the distal end of the catheter shown in FIG. 7A;

FIG. 8A is a longitudinal cross section of a fourth embodiment of the present disclosure including a two lumen catheter;

FIG. 8B is an enlarged view of the distal end of the catheter shown in FIG. 8A;

DETAILED DESCRIPTION

Figure 3:
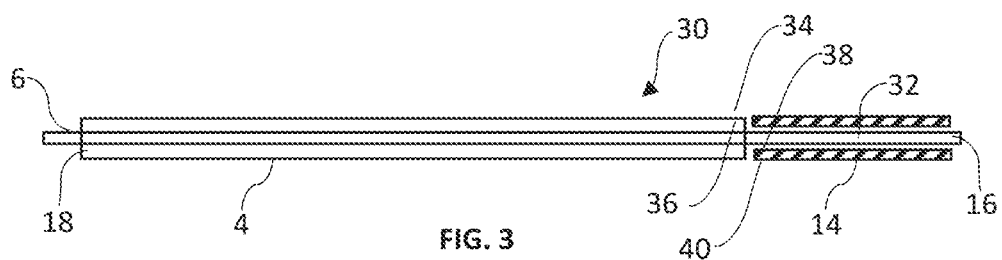
FIG. 3 is a longitudinal view of a coaxial catheter assembly.

A standard microcatheter for drug delivery is designed to access small vasculature and necessarily has a small outer diameter in the range of 0.5 mm to 2 mm more optimally 0.75 mm to 1 mm. For use in the peripheral vasculature, and in particular for tumor embolization, delivery catheters are typically 75 cm to 175 cm in length. Once the catheter is oriented at a target site within the blood vessel, drug, embolic agents, contrast or other fluids are injected through a lumen that extends longitudinally from proximal to distal ends. It is common that the fluids are viscous and must be injected at high flow rates in the range of 1 ml/second to 10 ml/second. However, flow rate is limited by injection lumen diameter or cross sectional area, length and the ability of the catheter wall to withstand high pressures in the range of 250 psi to 2000 psi, more typically in the range of 500 psi to 1,500 psi. Given that the catheter length is fixed by the requirements of the transvascular procedure, flow rate can be maximized by making the injection lumen and injection pressure tolerance as high as possible.

When considering a balloon microcatheter, an additional lumen that extends longitudinally from proximal to distal ends of the catheter is added for balloon inflation and deflation. In many embodiments, it is optimal for the balloon to inflate and deflate in as short a time as possible and in the range or 10 seconds to a maximum of 60 seconds. When balloons occlude or dilate blood vessels, it can be necessary for deflation to occur rapidly to avoid complications. Often the balloon is inflated with radiopaque contrast which is a viscous fluid. Therefore, it is desirable that the balloon inflation lumen also be as large as possible.

Since microcatheters have small cross sections, it is a challenge to achieve both rapid drug injection speed, which favors large injection lumen size, and rapid balloon inflation and deflation times, which favor large balloon lumens.

Further, it would be highly desirable for the mounted balloon not to increase the outer diameter of the catheter since it needs to maintain a small profile and it is optimal to mount the balloon so that in its retracted configuration it does not extend beyond the outer diameter of the catheter.

Transvascular microcatheters should also be flexible, most importantly at the location of the balloon which is mounted at the distal portion of the catheter to allow them to advance through tortuous vasculature. Balloon bonding adhesives tend to be rigid and measures should be taken to construct the balloon bonding surfaces to be flexible.

Therefore, in many embodiments, optimal characteristics of a balloon micocatheter include: 1) a large drug injection lumen, 2) a large balloon inflation lumen, 3) a catheter that withstands high pressure, and 4) a flexible distal catheter portion.

Strong bonding of the balloon to the catheter is also important to prevent detachment during a medical procedure and to assure that post inflation, the balloon can return to a position below the surface of the outer diameter of the catheter.

The methods and devices disclosed herein solve the aforementioned challenges and enable a balloon microcatheter to be adapted to include a large injection lumen, a large balloon inflation lumen, a flexible distal catheter portion and strong balloon bonding that assure the balloon will return to a retracted diameter less than that of the catheter's outer diameter.

The device of the present disclosure provides a means to affix a balloon to a catheter such that the balloon bonds are positioned below the surface (i.e. radially inward of the outside diameter) of the catheter assembly and, if desired, the balloon in its uninflated configuration can be positioned below the outer surface of the catheter assembly. The present device allows a balloon to be inflated from below the surface of a catheter assembly and when deflated, return thereto. Such a balloon catheter assembly, as disclosed herein, has a small profile, a strong attachment of the balloon to the catheter and rapid inflation and deflation times even with viscous solutions.

Referring to FIG. 1, a longitudinal cross section of the distal end of one embodiment of the present disclosure is shown with catheter assembly 2, outer catheter 4, inner catheter 6, inner catheter extension 8, outer adapter 10, support sheath 12, balloon 14, inner catheter lumen 16, annular lumen 18, fluid channel 20, proximal balloon bond 22, and distal balloon bond 24. In this embodiment, a coaxial catheter design is shown with outer catheter 4, having a proximal end and a distal end and a diameter larger than inner catheter 6, also having a proximal end and a distal end, whereby inner catheter 6 is positioned longitudinally inside of outer catheter 4. Inner catheter 6 extends distally beyond the distal end of outer catheter 4, as indicated by extension distance 8, said inner catheter extension providing a reduction in diameter whereupon a balloon or accessory can be attached.

Inner catheter 6 and outer catheter 4 are each typically composed of a laminate or composite of at least two layers, with a steel or other braid, coil, woven, and/or reinforcing material positioned between the layers or forming one of the layers. In some embodiments, a reinforcing material is molded within a less rigid base material such that the reinforcing layer is embedded in an encapsulation layer. This construction is provided to allow kink resistance and strength to withstand high pressure injection. Given the multi-layer construction, these walls typically have a thickness of 0.1 mm to 1 mm which consumes radial area which could otherwise be used to increase the size of the injection lumen or balloon inflation lumen. Therefore, thin wall construction is optimal, provided that strength, kink resistance and a tolerance to high pressure is maintained. In this exemplary embodiment, outer adapter 10 is composed of a single layer flexible material such as Pebax, polyamide, polyethylene, polyurethane or the like and has a wall thickness of 0.0001 mm to 0.01 mm, more typically 0.001 mm to 0.0050 mm, said thickness being less than that of the inner catheter or outer catheter. In some embodiments, the outer catheter 4 has a wall thickness of about 0.0635 mm and the outer adapter 10 has a wall thickness of about 0.00635 mm. In some embodiments, the wall thickness of the outer adapter 10 is no more than about 15% of the wall thickness of the outer catheter 4. The thickness and material type is different from that of the outer catheter and optimized for maximizing balloon inflation and injection lumen diameters, flexibility and bondability of the balloon material to the adapter.

The proximal end of outer adapter 10 is circumferentially oriented about the outer surface of the distal end of outer catheter 4 and steps centrally to a reduced diameter at a point distal to the distal end of outer catheter 4, said reduced diameter is circumferentially oriented about inner catheter 6. At its proximal end, support sheath 12 is positioned over the distal end of outer catheter 4 and the proximal end of outer adapter 10, and the distal end of support sheath 12 is positioned over the proximal end of balloon 14. Support sheath 12 compresses the proximal end of balloon 14 into the space below the other diameter of outer catheter 4, assuring that the balloon will return to a position below the outer diameter of outer catheter 4 and strengthens balloon bond 22 on outer adapter 10. In this exemplary embodiment, support sheath 12 is composed of a single layer flexible material with substantially the same wall thickness and material composition as the outer adapter 10.

The proximal end of inner catheter 6 is in fluid communication with the distal end of inner catheter 6 by way of inner catheter lumen 16. A space between outer catheter 4 and inner catheter 6 defines a generally annular lumen 18, and a space between the reduced diameter of outer adapter 10 and inner catheter 6 defines fluid channel 20. Balloon 14 is bonded at its proximal end to the reduced diameter of outside adapter 10 by proximal balloon bond 22, and the distal end of balloon 14 is bonded to inside catheter 6 at distal balloon bond 24, such that proximal balloon bond 22 and distal balloon bond 24 are radially inward from the outside diameter of outer catheter 4. In this exemplary embodiment, proximal balloon bond 22 and distal balloon bond 24 are also radially inward from the inside diameter of outer catheter 4, as shown in FIG. 1. The proximal end of catheter assembly 2 is in fluid communication with the interior volume of balloon 16 by way of annular lumen 18, and fluid channel 20. In some embodiments, inner catheter 6 may be located in an offset manner within outer catheter 4 such that the inflation lumen formed therebetween is crescent-shaped rather than annular.

The aforementioned disclosure enables a balloon microcatheter to be adapted to an optimal: small outer diameter for use in small vessels, flexibility to navigate in tortuous vasculature, high pressure tolerance to allow high flow rates of drug and contrast, short balloon inflation and deflation times, balloon bondability, balloon bond strength and maintenance of the balloon outer diameter to remain below the outer diameter of the outer catheter, even after balloon inflation and deflation.

Referring to FIG. 2 an axial cross section of a coaxial catheter assembly with outer catheter 4, inner catheter 6, inner catheter lumen 16 and annular lumen 18 defining a space between outer catheter 4 and inner catheter 6. Inner catheter lumen 16 extends from the proximal end of the outer catheter 4 to the distal end of the outer catheter 4 and allows fluid communication therebetween. Annular lumen 18 extends from the proximal end of the catheter assembly to the inner volume of a balloon and allows fluid communication to inflate and deflate the balloon.

Referring to FIG. 3, a longitudinal cross section of catheter assembly 30 is shown with outer catheter 4, inner catheter 6, inner catheter lumen 16, annular lumen 18, inner catheter extension 32, external catheter surface 34, internal catheter surface 36 (i.e. a portion of the inside diameter of outer catheter 4), inner balloon surface 38 and outer balloon surface 40. Outer catheter 4 has a diameter greater than inner catheter 6 and has a length that is less than that of inner catheter 6. Annular lumen 18 defines a space between outer catheter 4 and inner catheter 6 and extends from the proximal end of catheter assembly 30 to the inner volume of balloon 14 and allows fluid communication to inflate and deflate the balloon. Inner catheter 6 has a length that is greater than that of outer catheter 4 and a lumen 16 that extends from the proximal end of catheter assembly 30 to the distal end of catheter assembly 30 and allows fluid communication therebetween. Inner catheter extension 32 with a diameter less than that of outer catheter 4, provides a surface whereby a balloon or other accessory can be attached with the bonding surfaces below the surface of (i.e. radially inward from the outside diameter of) outer catheter 4 and, if desired, the balloon or other accessory can be positioned such that its outer diameter is below the surface of outer catheter 4. In some embodiments, the balloon bonding surface may also be radially inward from the inside diameter of outer catheter 4. External catheter surface 34 defines a circumferential area on the outside of the distal end of outer catheter 4 whereupon adapters and sheaths can be affixed, and internal catheter surface 36 defines a circumferential area on the inside of the distal end of outer catheter 4 whereon adapters can be affixed. The diameters of external catheter surface 34 and internal catheter surface 36 are equal to the outer diameter and inner diameter of the catheter selected, respectively, typically from 0.3 mm to 5 mm, and the longitudinal length of the fixation surfaces can be from 0.2 mm to 25 mm, more typically from 1 mm to 10 mm.

Figure 4A:
FIG. 4A is a side view of an outer adapter component.

Referring to FIG. 4A, a longitudinal cross section of an outer adapter 10 is shown with a diameter reduction between a large diameter surface 42 and a small diameter surface 44. Although outer adapter 10 shows a single step from large diameter surface 42 to small diameter surface 44, the transition can be configured with 2, 3, 4 or more steps or the transition can be a gradual as in a conical adapter. The outer adapter 10 provides a connection between the external catheter surface 34, of outer catheter 4 and an inner balloon surface 38 of balloon 14, providing fluid communication between the annular lumen 18 and the inner surface of balloon 14, whereby a proximal balloon bond is positioned between inner balloon surface 38 of balloon 14 and small diameter surface 44 of outer adapter 10, positioning the balloon bond below the surface of the outer diameter of outer catheter 4. In some embodiments, the outer adapter 10 is made from a plastic polymeric material such as polyester, nylon, Pebax, polyethylene, polyurethane, or other convenient material. In many embodiments, a thin wall is preferred; however any thickness can be used depending on the application. Material thickness will typically range from 0.0003 mm to 1 mm, more typically from 0.003 mm to 0.01 mm. The large diameter surface 42 of outer adapter 10 is typically glued, heat bonded, compressed or reflowed into the external catheter surface 34 of outer catheter 4. Reflow has the advantage that large diameter surface 42 of outer adapter 10 melts into the outer surface of outer catheter 4 at external catheter surface 34 and does not increase the diameter of outer catheter 4. The diameters of the large diameter surface 42 and the small diameter surface 44 will be dependent on the catheter diameter and the desired positioning of the balloon bonding surface below the outer diameter of outer catheter 4. Typically the outer diameter of medical catheters range from about 0.25 mm to 10 mm, more typically from 0.5 mm to 5 mm, thereby making the large diameter surface 42 of the outer adapter 10 range from about 0.5 mm to 4 mm. The outside adapter 10 can be any length of convenience, typically 2 mm to 25 mm, more typically 4 mm to 10 mm. The outer adapter 10 of the present disclosure is particularly useful in micro-catheters that commonly have small outer diameters in the range of 0.5 mm to 1.5 mm and are used for access into the peripheral vasculature and into small blood vessels. In this instance, it is important to keep the outer diameter of the catheter as small as possible. If a balloon or other accessory is placed on the catheter, it can be a significant advantage to bond or otherwise mount the accessory below at least the outer surface of outer catheter 4. In addition to a balloon, an accessory can include a tissue anchor, blade, mechanical occlusion device, partial occlusion device, a device to trap embolic particles, or any device of use in the vasculature.

Figure 4B:
FIG. 4B is a side view of an inner adapter component.

Referring to FIG. 4B, a longitudinal cross section of an inner adapter 46 is shown with a diameter reduction between a large diameter surface 48 and a small diameter surface 50. In some embodiments, inner adapter 46 is used instead of outer adapter 10. Although inner adapter 46 shows a single step from large diameter surface 48 to small diameter surface 50, the transition can be configured with 2, 3, 4 or more steps or be a gradual transition as in a conical adapter. The inner adapter provides a connection between the internal catheter surface 36 of an outer catheter 4 and balloon 14 at inner balloon surface 38, thereby positioning the balloon bonding surface or accessory attachment surface below the outer surface and the inner surface of outer catheter 4. The composition, measurements, use and benefits are as stated for FIG. 4A.

Figure 4C:
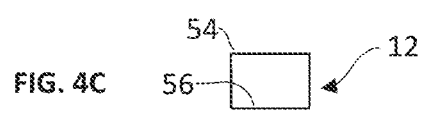
FIG. 4C is a side view of a support sheath component.

Referring now to FIG. 4C, a longitudinal cross section of a support sheath 12 is shown with a proximal end, a distal end, an outer surface 54 and an inner surface 56. The support sheath 12 fits circumferentially over the outer catheter 4 at external catheter surface 34 and balloon 14 at outer balloon surface 40. Support sheath 12 functions to strengthen the balloon bond and, if desired, hold the proximal end of balloon 14 at or below the outer surface of outer catheter 4. The length from proximal to distal ends of the support sheath is typically from 1 mm to 10 mm, more typically from 3 mm to 6 mm and any portion of the length can be bonded to the catheter with the remainder extended over the balloon or other accessory. In some embodiments, the support sheath has a length that is at least as great as the outside diameter of the distal end of the outer catheter. Typically the support sheath 12 is compressed, glued, reflowed or otherwise affixed to the outer catheter and extends over, but may not be attached to a balloon or other accessory. In some embodiments, the support sheath is made from polymeric material such as silicone, latex, polyester, nylon, Pebax, polyethylene, polyurethane, or other convenient material. In many embodiments, a thin wall is preferred, however, any thickness can be used depending on the application. Optimally the support sheath 12 is a heat shrink material that is placed at a desired position over the catheter and balloon, or other accessory, and heated, causing the material to reduce in diameter and compress about the surface of the outer catheter 4 and balloon 14. The thickness will typically range from 0.003 mm to 0.05 mm, more typically from 0.006 mm to 0.01 mm. Reflow and compression have the advantage that the outer surface 54 of the support sheath 12 melts or is compressed into the outer surface of the outer catheter 4 and does not increase the diameter of the outer catheter. The diameter of support sheath 12 is dependent on the catheter diameter. Typically the outer diameter of medical catheters range from about 0.5 mm to 5 mm.

Figure 5A:
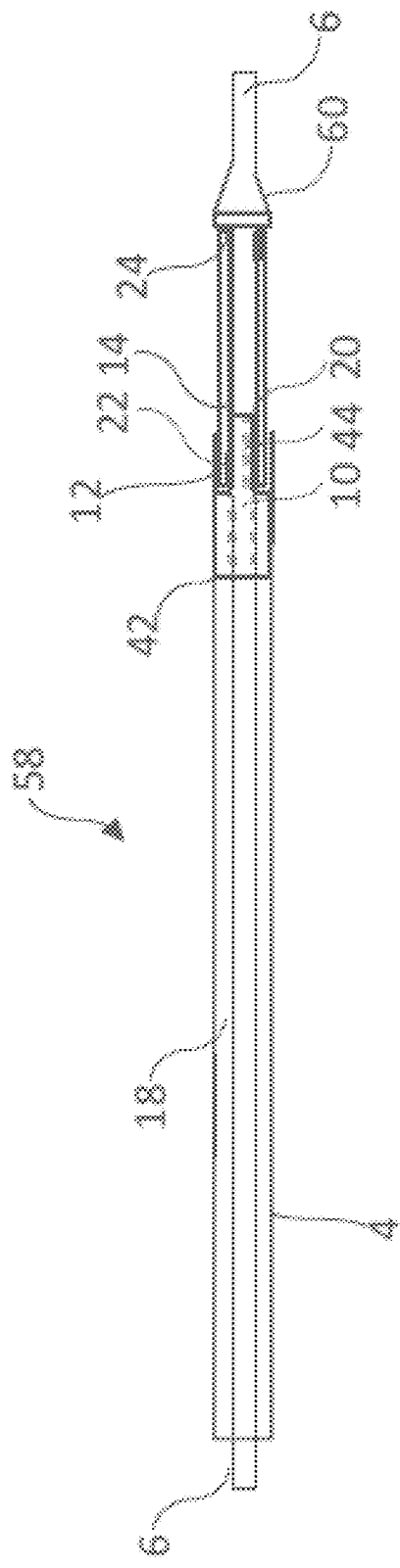
FIG. 5A is a longitudinal cross section of one embodiment of the present disclosure including a nose cone.
Figure 5B:
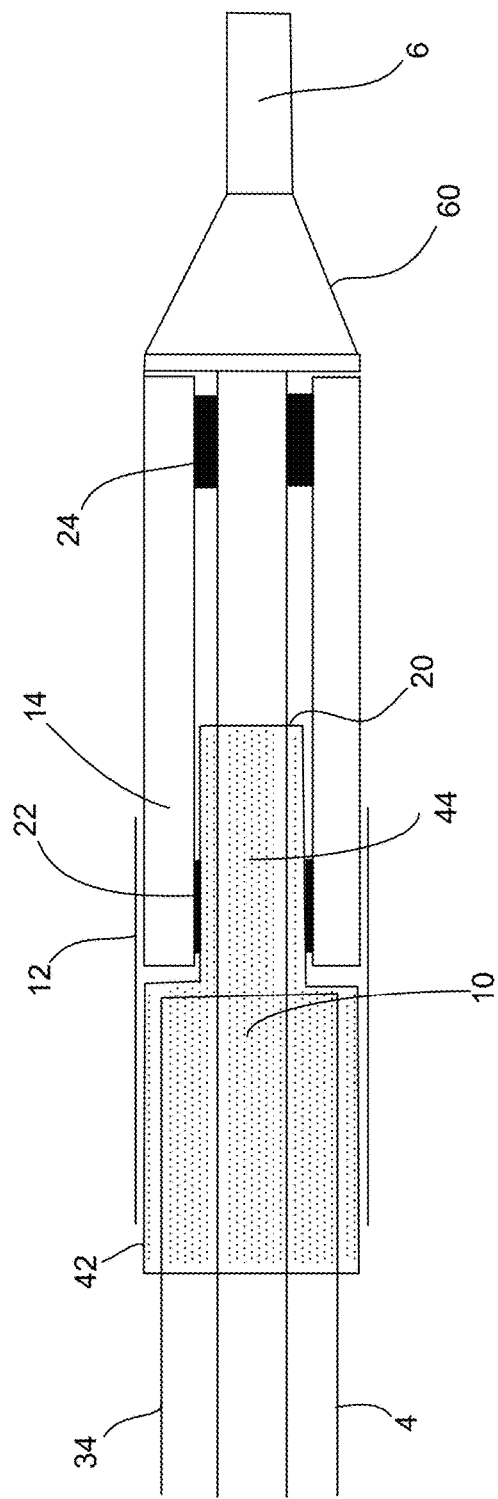
FIG. 5B is an enlarged view of the distal end of the catheter shown in FIG. 5A.

Referring now to FIGS. 5A and 5B, a longitudinal cross section of a second embodiment of the present disclosure is shown with catheter assembly 58, outer catheter 4, inner catheter 6, outer adapter 10, large diameter surface 42, small diameter surface 44, support sheath 12, nose cone 60, fluid channel 20, balloon 14, proximal balloon bond 22 and distal balloon bond 24. External catheter surface 34 of catheter 4 is bonded to the inner surface of the large diameter surface 42 of adapter 10. The inner surface of balloon 14 is bonded at its proximal end to the outer surface of small diameter surface 44 of adapter 10, at proximal balloon bond 22 and its distal end is bonded to inner catheter 6 at distal balloon bond 24 that is positioned proximal to nose cone 60. Support sheath 12 is positioned such that it extends over external catheter surface 34 of outer catheter 4 and the proximal end of balloon 14. The proximal end of support sheath 12 can be bonded, reflowed, compressed or otherwise affixed to external catheter surface 34 of outer catheter 4 and/or large diameter surface 42 of outer adapter 10, and the distal end of support sheath 12 is positioned over the proximal end of balloon 14 with the advantage of strengthening the balloon bond 22 and, if desired, holding balloon 14 below the surface of outer catheter 4. Support sheath 12 can be affixed to external catheter surface 34 and the proximal end of balloon 14, or it may not be affixed to one or both surfaces, provided that it does not move with respect to outer catheter 4 or balloon 14. Inner catheter 6 extends beyond the distal end of outer catheter 4 and nose cone 60 is affixed to inner catheter 6 at a location distal to the distal end of outer catheter 4. In this embodiment, the balloon sits in a pocket between the distal end of outer catheter 4 and the proximal end of nose cone 60 with the advantage of positioning the balloon bond lower than (i.e. radially inward from) the outer diameter of outer catheter 4 and, if desired, the balloon outer diameter, when in its unexpanded configuration, can be positioned so that it is substantially equal to or less than the outer diameter of the outer catheter 4. In this manner, a balloon, when in its unexpanded configuration, can be positioned within a pocket at or below the outer surface of outer catheter 4, expand to a diameter greater than outer catheter 4, and then return, upon deflation, to a diameter less than or equal to the outside diameter of outer catheter 4. The proximal end of catheter assembly 58 is in fluid communication with the interior space of balloon 14 by way of annular lumen 18 and adapter 10 at fluid channel 20 which is defined by an annular space between the inner surface of small diameter surface 44 of adapter 10 and the outer surface of inner catheter 6. Alternate configurations of this embodiment include use of adapter 10 and without the support sheath 12 or use of the support sheath 12 without the adapter 10. When only the support sheath 12 is used, the outer diameter of proximal balloon 14 is bonded to the inner surface of the support sheath 12. Another configuration of this embodiment includes the use of an outer adapter to affix the balloon to the nose cone 60 or the use of a support sheath to affix balloon 14 to nose cone 60 or the use of both an adapter and support sheath to affix balloon 14 to nose cone 60. Optimally, balloon 14, adapters, support sheaths and none cone 60 have an outer diameter equal to or less than the outer diameter of outer catheter 4.

Referring to FIGS. 6A and 6B, a third embodiment of the device of the present disclosure is shown with catheter assembly 62, outer catheter 4, inner catheter 6, outer adapter 10, large diameter surface 42, small diameter surface 44, support sheath 12, fluid channel 20, balloon 14, proximal balloon bond 22, distal balloon bond 24, second outer catheter 64, distal outer adapter 66, large diameter surface 68, small diameter surface 70 and second support sheath 72. Inner catheter 6 extends beyond the distal end of outer catheter 4 and second outer catheter 64 may be affixed to inner catheter 6 at a location distal to the distal end of outer catheter 4, whereby balloon 14 is disposed in a pocket between the distal end of outer catheter 4 and the proximal end of second outer catheter 64 with proximal balloon bond 22 and distal balloon bond 24 positioned below the surface of outer catheter 4 and second outer catheter 64. In one construction of the present embodiment, balloon 14 is configured with an outer diameter less than or equal to the outer diameter of catheter 4 and second outer catheter 64 and thereby is concealed within a pocket therebetween. When inflated to its radially expanded configuration, balloon 14 will have a diameter greater than the outside diameters of outer catheter 4 and second outer catheter 64 and extend radially outward from said pocket. When balloon 14 is then deflated from its radially expanded configuration it will return to a diameter less than or equal to outer catheter 4 and second outer catheter 64 and again be concealed within the pocket. The external catheter surface 34 at the distal end of outer catheter 4 is bonded to the inner surface of large diameter surface 42 of adapter 10. The proximal end of balloon 14 is bonded at its inner surface to the outer surface of small diameter surface 44 of outer adapter 10 and the distal end of balloon 14 is bonded at its inner surface to the outer diameter of small diameter surface 70 of distal second adapter 66. Alternately, the inner luminal surface of balloon 14 can be bonded at its distal end directly to inner catheter 6. The inner diameter of large diameter surface 68 of distal adapter 66 is bonded, reflowed, compressed or otherwise affixed to the proximal end of a second outer catheter 64. A flow channel between the inner surface of small diameter surface 70 of second adapter 66 and inner catheter 6 may or may not be present. In the case where one balloon is present the distal end of the balloon will be sealed. However, if a second balloon is positioned distal to a first balloon, then a flow channel may be configured to allow inflation and deflation of a second, third, fourth or any number balloons and it is understood that any number of balloons and outer catheter segments can positioned in series. A first support sheath 12 may be positioned such that it extends over the outer surface of the distal end of outer catheter 4 and the proximal end of balloon 14 and a second support sheath 72, may be positioned such that it extends over the outer surface of the proximal end of second outer catheter 64 and the distal end of balloon 14. Support sheaths 12 and 72 can be bonded, glued, reflowed, compressed or otherwise affixed to the distal end of outer catheter 4 or proximal end of second outer catheter 64 and may, if desired, be affixed to balloon 14. Support sheath 12 provides the advantage of restraining or compressing the proximal end of balloon 14 at the proximal balloon bond 22 and strengthening the balloon bond and preventing detachment. A second support sheath 72 adds the advantage of retaining or compressing balloon 14 at distal balloon bond 24 or strengthening the balloon bond and preventing detachment. The proximal end of catheter assembly 62 is in fluid communication with the interior space of balloon 14 by way of annular lumen 18 and outside adapter 10 at fluid channel 20, which is defined by an annular space between the inner surface of small diameter surface 44 of adapter 10 and the outer surface of inner catheter 6 as seen by flow path 26. Alternate configurations of this embodiment include an outer adapter 10 without a support sheath 12, a support sheath 12 without adapter 10, outer adapter 66 without second support sheath 72, second support sheath 72 without outer adapter 66 or any combination of adapters and support sheaths, provided that the proximal end and distal end of balloon 14 have at least one adapter or sheath or are bonded directly to inner catheter 6 and annular lumen 18 is in fluid communication with the interior surface of balloon 14. Optimally, balloon 14, both support sheaths and both adapters have an outer diameter equal to or less than the outer diameters of outer catheter 4 and second outer catheter 64 of catheter assembly 62, although there is no requirement for balloon 14 to be constrained below the surface of catheter assembly 62, provided that bonding surfaces 22 and/or 24 are positioned below the outer surface of catheter assembly 62. It would be particularly useful when delivering therapy in small vessels, for a balloon or other accessory or tool to be positioned below the surface of a catheter, in its unexpanded state, and then following inflation or deployment be returned to the same position below the catheter surface.

Referring now to FIGS. 7A and 7B, a longitudinal cross section of yet another embodiment of the present disclosure is shown with catheter assembly 74, outer catheter 4, inner catheter 6, proximal inner adapter 46, large diameter surface 48, small diameter surface 50, fluid channel 76, distal inner adapter 78, large diameter surface 80, small diameter surface 82 and support sheath 86. In this embodiment, inner adapters 46 and 78 are used instead of outer adapters whereby the outer surfaces of large diameter surfaces 48 and 80 of inner adapters 46 and 78 are bonded or otherwise affixed to the inner circumference of outer catheter 4 and the inner circumference of second outer catheter 84. In this embodiment, the balloon 14 is disposed in a pocket between the distal end of outer catheter 4 and the proximal end of second outer catheter 84. It is understood that any combination of adapters and support sheaths can be used. The proximal and/or distal balloon bonds are positioned below the outer surfaces of outer catheter 4 and second outer catheter 82 and fluid communication is maintained from the proximal end of catheter assembly 74 and the interior surface of the balloon 14 by way of annular lumen 18 and adapter 46 at fluid channel 76 which is defined by an annular space between the inner surface of small diameter surface 50 of adapter 46 and the outer surface of inner catheter 6. It is also understood that a nose cone or other nose piece can be affixed to a location distal to the second outer catheter 84 and that any number of balloons and outer catheter segments can be serially oriented along catheter assembly 74.

Referring now to FIGS. 8A and 8B, yet another embodiment of the present disclosure is shown with catheter assembly 88, two lumen catheter 90, injection lumen 92, balloon inflation lumen 94, injection lumen extension 96, nose cone 98, outer adapter 100, large diameter surface 102, small diameter surface 104, support sheaths 106 and 108, balloon 110, proximal balloon bond 112, distal balloon bond 114, fluid channel 116 and flow path 118. In this instance, a single catheter with 2 lumens is used instead of the two catheter coaxial construction as described in the above embodiments. While a two lumen catheter is useful for numerous applications, the catheter can also include 3, 4, 5 or more lumens as needed. Catheter assembly 88 can be any length useful for medical applications, typically from 25 cm to 250 cm, more typically from 50 cm to 150 cm. Injection lumen 92 has a proximal end and a distal end and extends from the proximal end of catheter assembly 88 to the distal end of catheter assembly 88 and provides fluid communication therebetween. Balloon inflation lumen 94, has proximal and distal ends and extends from the proximal end of catheter assembly 88 to balloon 110, providing a means for inflation and deflation. Injection lumen 92 extends distally beyond the distal end of two lumen catheter 90 and distally beyond the end of balloon lumen 94 as illustrated by injection lumen extension 96 and length 120. The injection lumen extension typically has a length in the range of 0.1 cm to 50 cm, more typically from 1 cm to 10 cm. Nose cone 98 is positioned about the injection lumen extension 96 at a point that is distal to the distal end of two lumen catheter 90, whereby balloon 110 is disposed in a pocket between the distal end of two lumen catheter 90 and the proximal end of nose cone 98. Nose cone 98 is typically placed at a distance of 0.25 cm to 10 cm, more typically from 1 cm to 3 cm from the distal end of two lumen catheter 90 and can be any shape or configuration and can be composed of any convenient material including materials that are radiopaque. For illustration only, the embodiment of FIGS. 8A and 8B includes outer adapter 100 and both proximal and distal support sheaths 106 and 108, however any combination of adapters and support sheaths can be used, provided that fluid communication is maintained between the inflation lumen 94 and the interior surface of balloon 110. Outer adapter 100 has a large diameter surface 102 and a small diameter surface 104, whereby the inner surface of large diameter surface 102 is bonded to the distal outer surface of two lumen catheter 90 and the small diameter surface is oriented about injection lumen extension 96, such that an annular space between the inner surface of small diameter surface 104 and injection lumen extension 96 is maintained. The proximal end the catheter assembly 88 is in fluid communication with the interior space of balloon 110 by way of balloon inflation lumen 94, outer adapter 100, an annular space between the injection lumen extension 96 and the inner surface of the small diameter surface 104 of adapter 100, defined by fluid channel 116 and flow path 118. In most cases it is desirable that the central injection lumen 92 allow fluid communication therethrough, however, this is not a requirement. In some uses, the injection lumen 92 can be a solid and without fluid communication, thereby configuring a one lumen balloon catheter. It may also be desirable for balloon 110 to sit below the outer diameter of catheter assembly 88, however this is not required. In some embodiments, balloon 110 does not sit below the outer diameter of catheter assembly 88, but at least the proximal balloon bond 112 is positioned below the outer diameter of catheter assembly 88.

Figure 9A:
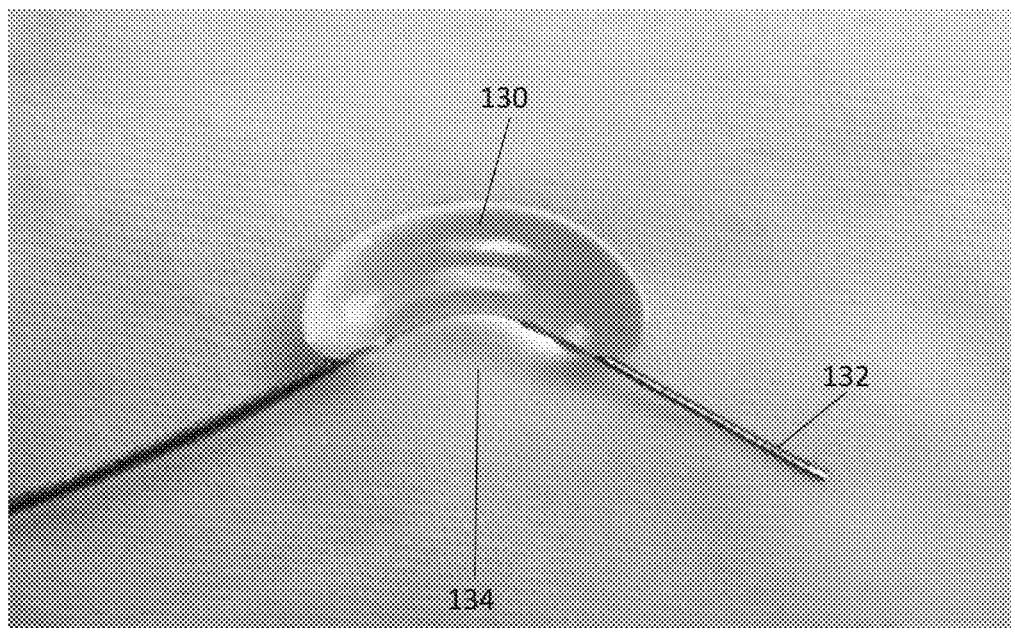
FIG. 9A is a side view of a catheter balloon inflated to the extent that it laterally deflects the distal tip of the catheter for steering.
Figure 9B:
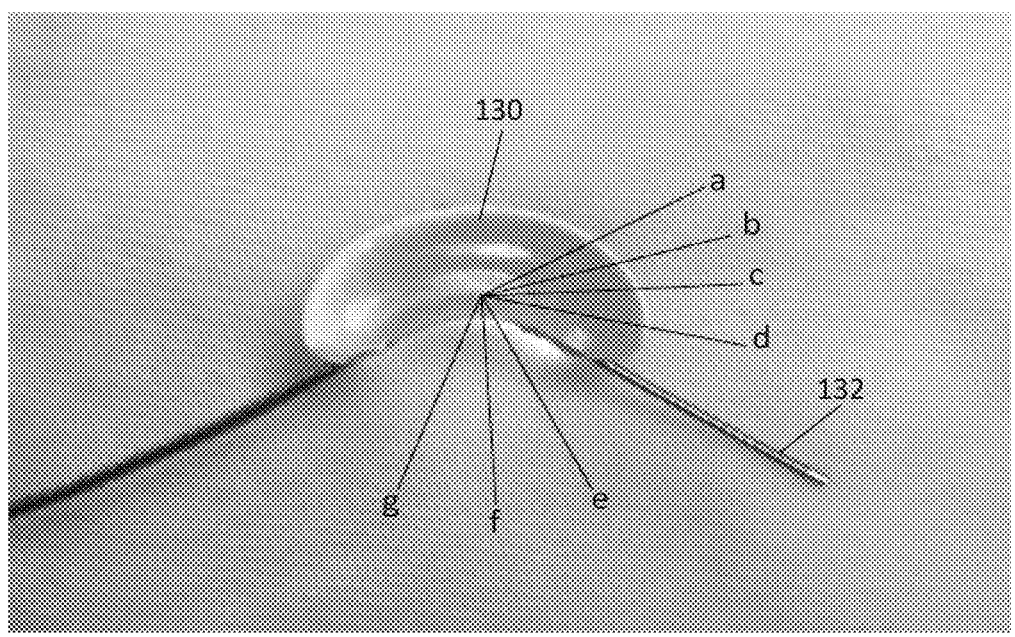
FIG. 9B is the same as FIG. 9A with markings added to show various deflection angles.

Referring now to FIGS. 9A and 9B, an embodiment is shown comprising a balloon mediated steerable catheter. As shown in FIG. 9A, a catheter tip may be provided with a balloon 130 near its distal tip 132, similar or identical to the configurations previously described. The balloon 130 may be inflated as shown past a diameter needed to occlude a small blood vessel such that it bulges laterally to one side of the catheter tip 132 as shown. This off-center state of balloon 130 forces the distal tip 132 of the catheter to bend laterally in the opposite direction around a "bend point" 134. The degree of bend or bend angle of distal tip 132 is a function of the volume of fluid in balloon 130. This arrangement can be used as a means to steer a catheter around a sharp turn.

FIG. 9B depicts various angles that catheter tip 132 may bend away from the longitudinal axis of the main catheter. As balloon 130 is progressively inflated with more fluid, tip 132 may bend from a straight orientation (a) through various acute angles (b), (c) and (d), to a right angle (e) and to obtuse angles (f) and (g), as shown.

According to some embodiments, a protocol for advancing the catheter around a sharp turn comprises the following steps:
1) track the catheter over a guidewire to the vascular branch or sharp angle;

2) withdraw the guidewire just enough to position the distal tip of the guidewire to a position proximal to the catheter bend point 134;
3) inflate the balloon 130 and visualize the direction that the catheter tip 132 is bending, such as by using fluoroscopy;
4) rotate the catheter axially such that tip 132 is pointed in the desired direction;
5) further inflate or deflate balloon 130 until catheter tip 132 is pointed into the desired branch artery;
6) advance the guidewire into the branch artery;
7) advance the catheter over the guidewire into the branch artery; and
8) deflate the balloon and continue to advance the catheter over the guidewire.

In some protocols, a contrast agent can be injected through the distal tip 132 of the catheter and fluoroscopy can be used to visualize the target vessel.

Balloon 130 may be configured with a uniform wall thickness, or it may be provided with a thinner wall thickness on one side to ensure that it inflates laterally to the same side every time. In some embodiments, the wall thickness may be varied to provide a desired shape or inflation profile. In some embodiments the balloon is configured to surround the circumference of the catheter, and in other embodiments it can be attached to only one side of the catheter. In embodiments that utilize a balloon that surrounds the catheter, an adhesive may be used between one side of the catheter and part of the inside surface of the balloon to ensure that the balloon does not inflate on that side.

In some embodiments, bend point 134 is the midpoint of a curve. The curve may have a radius of 50 mm, 25 mm, 10 mm or less. The catheter may be modified at bend point 134 to allow the catheter to bend with less force applied by balloon 130. For example, the catheter may have a reduced diameter and/or wall thickness at one or more locations to facilitate easier bending and/or a smaller radius of curvature. In some embodiments, the bend point can be varied by advancing or retracting a guidewire within the catheter, such that the catheter starts bending just beyond the distal end of the guidewire.

As used herein, the word "about" means plus or minus 10% of a nominal value, unless the particular context indicates otherwise. In view of the teachings herein, many further embodiments, alternatives in design and uses of the embodiments of the instant disclosure will be apparent to those of skill in the art. As such, it is not intended that the invention be limited to the particular illustrative embodiments, alternatives, and uses described above but instead that it be solely limited by the claims presented hereafter.

What is claimed is:

1. A method of using a balloon catheter assembly, the method comprising:
   providing a balloon catheter assembly, the assembly comprising:
   an outer catheter having a proximal end and a distal end, the distal end of the outer catheter having a wall thickness, the outer catheter comprising at least two layers including a braided, coiled or woven reinforcing layer and a base layer, the outer catheter having an outer diameter that does not step down at the distal end of the outer catheter;
   an inner catheter located coaxially within a lumen of the outer catheter, the inner catheter having an injection lumen extending therethrough, the inner and outer catheters forming an inflation lumen therebetween;
   an outer adapter having a length less than 25 mm, a proximal end and a distal end, the proximal end of the outer adaptor being sized to fit over an outside surface of the distal end of the outer catheter and configured to be affixed thereto, the distal end of the outer adapter having a reduced outer diameter portion that is smaller than the outer diameter of the outer catheter at the distal end of the outer catheter, the distal end of the outer adapter having an inside diameter that is larger than an outer diameter of the inner catheter, thereby forming a fluid channel therebetween that is in fluid communication with the inflation lumen, the outer adapter having a wall thickness that is between 0.001 mm and 0.005 mm and is thinner than the wall thickness of the distal end of the outer catheter, the outer adapter not having a braided, coiled or woven reinforcing layer; and
   a balloon having a proximal end with an inner surface affixed to the reduced outer diameter portion of the outer adapter, the balloon having a distal end with an inner surface affixed to the outer diameter of the inner catheter, the balloon having an interior space that is in fluid communication with the fluid channel, the proximal end of the balloon being less than 25 mm away from the distal end of the outer catheter;
   inserting a distal end of the balloon catheter assembly into a blood vessel of a body;
   inflating the balloon by introducing a fluid through the inflation lumen and the fluid channel into the interior space of the balloon to at least partially occlude blood flow in the blood vessel;
   injecting a substance into the blood vessel through the injection lumen;
   deflating the balloon by removing the fluid from the interior space of the balloon such that the balloon returns entirely within a predetermined volume having an outer diameter substantially equal to or less than the outer diameter of the outer catheter at the distal end of the outer catheter; and
   withdrawing the distal end of the balloon catheter assembly from the blood vessel.

2. The method of claim 1, wherein the inner catheter has a distal end that extends distally beyond the distal end of the balloon.

3. The method of claim 2, wherein the balloon catheter assembly further comprises a nosecone located on the distal end of the inner catheter distal to the balloon, the nosecone having an outer diameter substantially equal to the outer diameter of the outer catheter at the distal end of the outer catheter such that the balloon is recessed in a pocket formed between the nosecone and the outer catheter when the balloon is in a deflated configuration.

4. The method of claim 1, wherein the balloon catheter assembly further comprises a proximal bond that affixes the inner surface of the proximal end of the balloon to the reduced outer diameter portion of the outer adapter, and a distal bond that affixes the inner surface of the distal end of the balloon to the outer diameter of the inner catheter.

5. The method of claim 4, wherein both the proximal bond and the distal bond are located radially inward from the outer diameter of the outer catheter at the distal end of the outer catheter.

6. The method of claim 5, wherein both the proximal bond and the distal bond are located radially inward from an inside diameter of the outer catheter at the distal end of the outer catheter.

7. The method of claim 1, wherein the inflation lumen has a substantially annular cross-section.

8. The method of claim 1, wherein the outer catheter comprises a base material and a different reinforcing material, and the outer adapter is made of a plastic polymeric material.

9. The method of claim 1, wherein the outer adapter has been attached to the distal end of the outer catheter using a reflow process.

10. The method of claim 9, wherein the outer diameter of the outer catheter at the distal end of the outer catheter has not been increased by the addition of the outer adapter after the reflow process.

11. The method of claim 1, wherein the balloon catheter assembly further comprises a support sheath disposed over and compressing the proximal end of the balloon.

12. The method of claim 11, wherein the support sheath is composed of a single layer flexible material with a wall thickness and a material composition that are the same as those of the outer adapter.

\* \* \* \* \*